United States Patent [19]
Kawchitch

[11] 3,983,878
[45] Oct. 5, 1976

[54] SURGICAL APPLIANCE

[76] Inventor: Claude Edward Kawchitch, Flat 1, 35 Bromby St., South Yarra, Victoria, Australia

[22] Filed: Nov. 27, 1974

[21] Appl. No.: 527,559

[30] Foreign Application Priority Data
Dec. 10, 1973 Australia............................ 5922/73

[52] U.S. Cl. .............................. 128/335; 24/201 C
[51] Int. Cl.² ........................................ A61B 17/08
[58] Field of Search ............ 128/334 R, 334 C, 335, 128/337; 24/201 C

[56] References Cited
UNITED STATES PATENTS

| | | | |
|---|---|---|---|
| 2,696,032 | 12/1954 | Sander .............................. | 24/201 C |
| 2,752,921 | 7/1956 | Fink ................................. | 128/334 R |
| 3,516,409 | 6/1970 | Howell .............................. | 128/335 |
| 3,863,640 | 2/1975 | Haverstock ........................ | 128/335 |

FOREIGN PATENTS OR APPLICATIONS

| | | | |
|---|---|---|---|
| 215,065 | 5/1961 | Austria .............................. | 128/335 |

Primary Examiner—Dalton L. Truluck
Attorney, Agent, or Firm—Ladas, Parry, Von Gehr, Goldsmith & Deschamps

[57] ABSTRACT

Appliance for sutureless closure of surgical incision comprises tape member and spring closure member. Tape member has adhesive on one side for fastening to skin of patient and pair of closely spaced longitudinal ribs on other side. Incision is made through tape member between ribs and spring member subsequently clasps ribs to provide sutureless closure. Spring member has straight side portions to grip ribs throughout substantial part of their length and is shaped so to contract laterally on axial compression to increase the grip.

14 Claims, 9 Drawing Figures

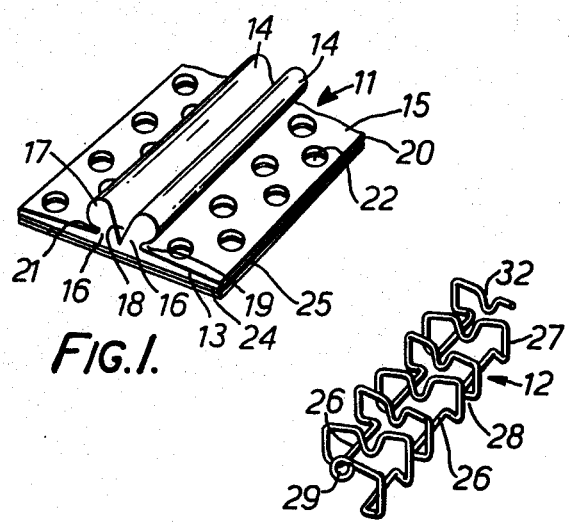
FIG. 1.
FIG. 2.
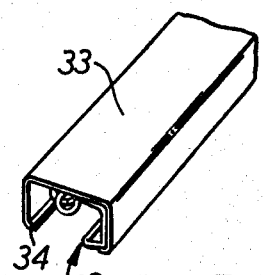
FIG. 3.
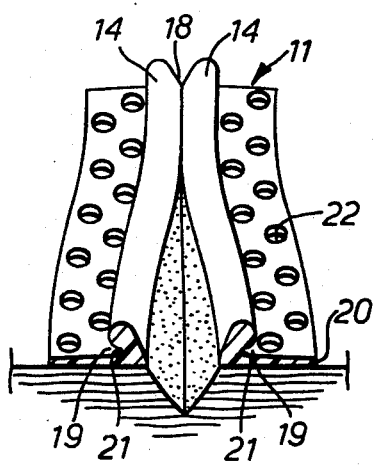
FIG. 4.
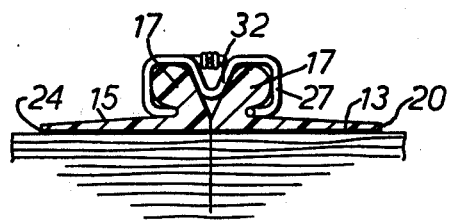
FIG. 6.
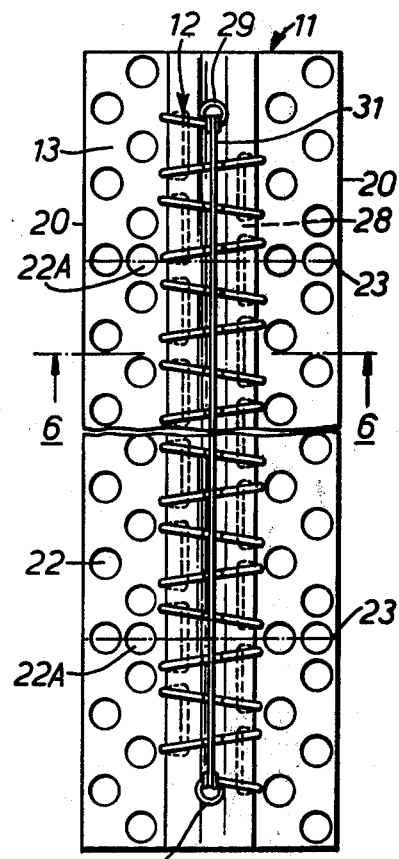
FIG. 5.

SURGICAL APPLIANCE

BACKGROUND OF THE INVENTION

FIELD OF THE INVENTION

The present invention relates to surgical appliances designed to provide sutureless closure of surgical incisions.

Description of the Prior Art

Various types of appliances have previously been proposed for providing sutureless closure of surgical incisions. For example British Pat. Specification No. 987,779 discloses an appliance in the form of an adhesive tape which is adhered to the skin over the area in which the incision is to be made. The tape is cut at the time of making the incision and is provided with means for drawing the cut edges of the skin together after the operation without suturing. Various means for completing the closure are suggested. The tape may be provided with two parallel ridges, one to either side of the incision which are brought together by suturing, welding or by using deformable metal clips. None of these methods ensures that the cut edges of the skin will be held together properly and the technique of suturing or welding is quite inconvenient. The present invention provides an improved appliance which enables the closure to be made very rapidly and which may be designed to ensure minimum movement of the skin edges relative to one another.

Other examples of sutureless closures are described in U.S. Pat. Nos. 3,698,395 and 3,516,409 and British Specifications No. 1,217,944 and 1,236,437. The applicance of United States Pat. No. 3,516,409 is essentially an adhesive tape formed in two halves which may be brought together by a zip fastener. When the incision is made the scalpel must be held against the slide of the zip fastener and the zip caused to open in advance of the scalpel. This would require considerable technique and the incision must follow the line of the fastener very accurately if the skin edges are to be brought together correctly by closure of the fastener after the surgery.

Moreover a zip fastener does not produce a sufficient closing action to ensure that the skin edges are brought together and held immobile relative to one another. The other proposals involve tying separated adhesive strip portions together at intervals along their length. Compared with the appliance of the present invention they are relatively clumsy in use and provide a less satisfactory closure.

SUMMARY OF THE INVENTION

The surgical appliance of the present invention comprises an elongate flexible tape member and an elongate spring member; said tape member having on one side an adhesive surface by which it can be adhered to the skin of a surgery patient and on the other side a pair of parallel ribs extending longitudinally of the tape member and defining between them a course along which to make an incision through the tape member and the skin beneath; said spring member comprising two sets of aligned straight side portions interconnected by connecting portions such that the spring member is of generally channel shaped configuration with said sets of straight side portions defining the mouth of the channel; and said spring member being applicable to the tape member such that the ribs project into said channel shape configuration of the spring member and are clasped between said sets of straight side portions.

Preferably, the ribs are shaped to define at their outer sides a pair of longitudinally extending and laterally outwardly facing channels for engagement with the two sets of straight side portions of the spring member when the spring member is applied to the tape member.

Preferably too, the straight side portions of each said set traverse a major proportion of the overall length of the set when the spring member is in its relaxed condition.

In order that the invention may be more fully explained some particular embodiments thereto will now be described in detail with reference to the accompanying drawings.

BRIEF DESCRIPTION OF THE DRAWINGS

FIG. 1 is a broken perspective view showing part of the tape member of one appliance constructed in accordance with the invention;

FIG. 2 is a broken perspective view showing part of a spring member of the appliance;

FIG. 3 is a perspective view of part of a dispenser which holds the spring member of FIG. 2 before the spring element is applied to the tape;

FIG. 4 is a partly sectioned view showing the manner in which the tape is applied to the skin of the patient and an incision made through it;

FIG. 5 is a plan of the appliance on completion of the sutureless closure;

FIG. 6 is a cross-section on the line 6—6 in FIG. 5;

DESCRIPTION OF THE PREFERRED EMBODIMENT

Figure 7:
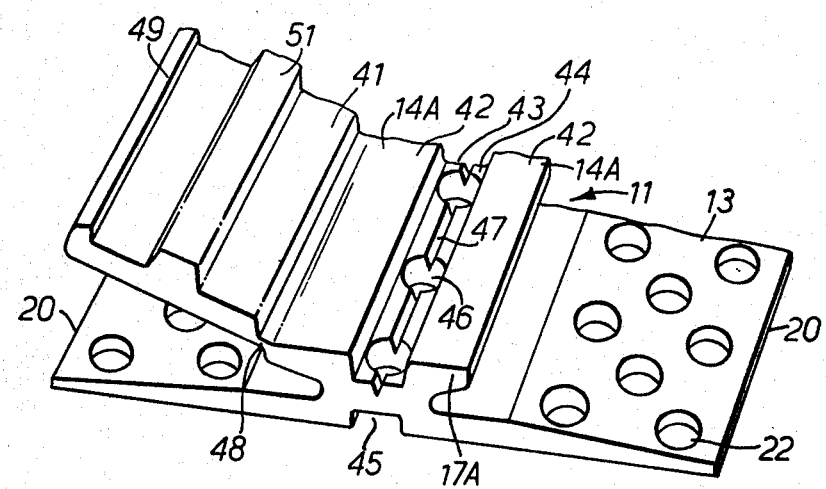
FIG. 7 is a broken perspective view of part of the tape member of an alternative form of appliance.

The surgical appliance illustrated by FIGS. 1 to 6 is comprised of a tape member 11 and an elongate spring member 12.

Tape member 11 comprises a flat strip 13 and a pair of ribs 14 projecting from one face 15 of the strip. Ribs 14 are closely spaced and parallel and they are located centrally of strip 13, i.e. midway between the longitudinal side edges 20 of the strip. The underface of strip 13 of the tape member is flat whereas the outer parts of face 15 slope slightly relative to the underface so that the strip portion tapers in thickness away from its central part to become thinner toward its side edges 20.

Ribs 14 are comprised of inner portions 16 by which they are connected to strip 13 and outer portions 17 which are in the form of solid cylindrical beads which project laterally outwardly of the inner portions. The inner connecting portions of the ribs are shaped such that a deep V-shaped channel 18 is defined between ribs 14 and a pair of laterally outwardly facing channels 19 extend along the outer sides of the ribs. More specifically channels 19 are formed between the outer head portions 16 of the ribs and the upper face 15 of strip 13 and they have semi-cylindrical roots 21.

Tape member 11 is moulded in one piece in a long length from a bio-compatible material such as silicon rubber. Strip 13 is perforated by holes 22, which, as indicated in FIG. 5, are arranged in two zig-zag patterns along the tape member one to either side of rib portions 14. At regular intervals along the tape member there are additional holes 22A and member 11 is formed so that transverse lines of weakness indicated by lines 23 are created. This may be achieved by lines of very small perforations through member 11 or by score lines formed during moulding of the member. The purpose of these lines of weakness is to enable the member to be readily separated along those lines so that lengths may be torn off for purposes to be explained below.

The flat underface of tape member 13 is coated with a film 24 of a strong bio-compatible adhesive to enable the tape member to be firmly adhered to the patient's skin. Cyano-methacrylate is one suitable adhesive. This adhesive film may be protected by a tear off cover sheet 25 of non-adhering plastic material such as polyethylene as indicated in FIG. 1.

Spring member 12 is formed from a single length of resilient spring wire which is bent to a complex tortuous shape. This shape is such that the spring member has two sets of longitudinally aligned straight side portions 26 which are interconnected by connecting portions 27 of generally channel shaped formation so that the overall configuration of the spring member conforms to a channel shape having an open mouth between the two sets of straight side portions 26. The two sets of straight side portions 26 are staggered relative to one another in the longitudinal direction of the spring member and connecting portions 27 are successively oppositely inclined to the longitudinal direction. More specifically each straight side portion which is overlapped in the longitudinal direction by a pair of straight portions of the other set has its two ends connected to the adjacent ends of that pair by a pair of mutually oppositely inclined connecting portions. The connecting portions 27 are angled such that in the relaxed condition of the spring member the gaps 28 between the straight side portions of each set 26 represent a little less than 20% of the total length transversed by that set 26, the remainder being occupied by the straight portions themselves.

An important consequence of the configuration of spring member 12 is that on longitudinal compression of that member to reduce or take up the gaps 28 connecting portions 26 serve as struts and the mutually oppositely inclined connecting portions 27 serve as links which rotate to cause the two sets of straight portions to be drawn toward one another laterally of the spring member, i.e. longitudinal compression of the spring member causes lateral contraction of the channel mouth between the two sets of straight members 26.

The two ends of spring member 12 are terminated by eyes 29 and as will be explained below longitudinal compression forces may be applied to the spring member by tying a thread 31 between these eyes. Connecting portions 27 have V-shaped tongues 32 formed in them along centreline of the spring member and projecting inwardly of the channel configuration of that member, i.e. toward the channel mouth which is defined between the two sets of straight portions 26.

As will be explained below spring member 12 is applied to tape member 11 with the aid of an applicator 33 which is illustrated in FIG. 3. This applicator is a channel-shaped element with inturned mouth flanges 34 and it is of such size that the spring member 12 is a neat fit within it and can be slid into it endwise.

In use of the illustrated appliance, the surgeon, after cleansing and preparing the skin in the area in which it is proposed to make an incision, takes a length of strip member 11 which is about 10 cm longer than the proposed incision length, tears away the protective sheet 25 and applies tape member to the skin with ribs 14 along the proposed line of incision. Channel 18 defined between ribs 14 then provides a course along which the surgeon makes the incision through the tape member and the skin beneath. FIG. 4 indicates the manner in which the tape member separates to allow the skin and underlying tissue to come apart along the incision.

The incision is closed by bringing the separated parts of the tape member together and applying spring member 12 around the ribs 14 to hold the tape portions together. As indicated by FIGS. 5 and 6 spring member 12 fits neatly around ribs 14 with its two sets of straight portions 26 engaged with the channels 19 extending along the sides of the ribs and with the V-shaped tongues 32 of connecting portions 27 engaged within the V-shaped channel 18 defined between the ribs. Spring member may be applied with the aid of applicator 33 simply by sliding the applicator with the spring member loaded within it over and along ribs 16 from one end of the strip member. Spring member 12 is formed so that in its relaxed condition the channel mouth between straight portions 26 is slightly narrower than the distance between the roots 21 of side channels 19 in tape member 11 so that as it is pushed onto the ribs by the applicator it grips them to such an extent that the applicator can simply be pulled away in the reverse direction and the spring member will remain in position to hold the ribs together. In the case of short incisions the holding action provided by the spring member simply by its natural gripping engagement with the ribs will be sufficient to provide adequate closure of the incision. However, to provide a firm closure, particularly in cases where the incision is long, thread 31 may be tied between the eyes 29 of spring member 12 and tightened to apply axial compression forces to the spring member. As explained above, this not only closes the gaps 28 but moves the two sets of straight side portions 26 toward one another which will provide increased gripping action.

The interaction between spring member 12 and tape member 11 is such that the two skin edges along the closed incision are firmly held against movement relative to one another over the complete length of the incision although the appliance can bend quite freely to permit normal skin movement. This is achieved by ensuring that the whole of the central part of tape member 11 including the two ribs 14 is held firmly together as a single entity so that it cannot change its tranverse cross-section. The spring member applies inward forces at the channel roots 21 parallel with the skin surface and because the central part of the tape member is held against change of cross-section the only forces applied to the skin at the area of the incision are the inward forces applied via the adhesive film in the plane of the skin. The tongue portions 32 of the spring member provide a reaction against inward forces exerted by straight portions 26 and ensure that the upper rib portions 17 do not move inwardly toward one another. It will be appreciated that such inward movement would cause forces transverse to the skin in the vicinity of the incision.

To ensure proper holding action on the central part of the tape member it is important that the straight portions 26 of the spring member be a tight (i.e. slight interference) fit within channels 19 and further that the spring member should provide a firm grip between the rims of the ribs and channels 19, i.e. that there be an interference fit between the spring member and the outer and inner areas of contact with the ribs.

When the incision has healed sufficiently for removal of the appliance, thread 31 is cut and spring member 12 is slid back out of engagement with ribs 14 and the tape member is simply stripped away from the skin. Solvent may be applied to the adhesive to assist in the stripping operation.

During healing of the incision holes 22 serve as ventilation and moisture escape passages. They also assist in applying the solvent to the adhesive film when the tape member is to be removed. If during healing any part of the incision should become infected an appropriate segment of the tape member may be removed between successive lines of weakness 32 to expose the infected area for treatment.

Figure 8:
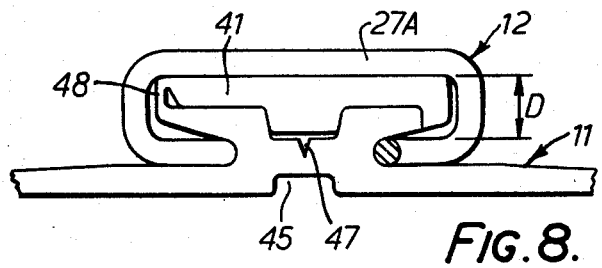
FIG. 8 is an end view of the alternative appliance with an end part of its spring member broken away.

FIGS. 7 and 8 illustrate a modified appliance constructed in accordance with the invention. This appliance is generally similar to that described with reference to FIGS. 1 to 6 and like parts have been identified by like reference numerals. As before, strip 13 is tapered in thickness so as to become thinner toward its side edges 20. For simplicity, the adhesive and protective films applied to the underface of strip 13 are not illustrated. In this case the central part of tape member 11 is modified considerably so that ribs 14A are of a different shape to those of the previous embodiment and a flap 41 is formed integrally with one of the ribs. The outer portions 17A of ribs 14A are shaped as laterally outwardly projecting flanges with flat rims 42. A channel 43 with a flat bottom 44 is defined between the ribs. Beneath channel 43 a channel 45 is formed in the underside of the tape member and a series of holes 46 is formed through the wall of the tape member between channels 43, 45. A small V-shaped groove 47 is formed in the flat bottom 44 of channel 43 along the length of tape member 11.

Ribs 42 are of differing widths and flap 41 is connected along one edge to the outer side edge of the wider of these ribs. The flap is formed integrally with the rib, being connected to the ribs by a reduced cross-section connecting portion 48 which provides a hinge connection allowing it to be swung down on to the flat rims 42 of the ribs. It has an outer edge flange 49 and a solid central tongue 51 and and when it is swung down on the rib rims central tongue 51 enters channel 43 and outer edge flange 49 engages outer side edge of the narrow flange 42 in the manner shown in FIG. 8.

Spring member 12A is the same as the spring member 12 of the appliance described with reference to the FIGS. 1 to 6 except that its connecting portions 27A do not have the V-shaped tongues 32.

In use of the appliance illustrated in FIGS. 7 and 8 V-shaped groove 47 defines a course along which the incision is made by a scalpel. When the incision is to be closed flap 41 is swung down to provide an initial holding action between the two ribs before spring member 12 is applied. Tongue 51 engages channel 43 to provide the reaction against the spring forces and preventing ribs 14 from moving toward one another. As before the straight portions 26 of the spring member engage channels 19 with a slight interference fit and there is also a slight interference fit between the spring and the upper and lower areas of contact with the ribs, i.e. the dimension indicated as D in FIG. 8 is slightly less for the spring than for tape member 11 when both are in their relaxed condition. Channel 45 serves as a drainage channel for the incision during healing. It is only about 1.5mm wide so that the unrestrained skin portions adjacent the incision are not large enough to allow separation or puckering.

Figure 9:
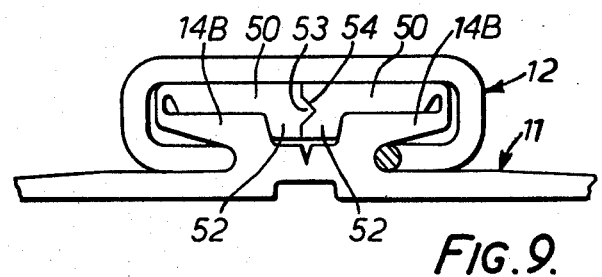
FIG. 9 is an end view of a still further form of appliance constructed in accordance with the invention with an end part of its spring member broken away.

FIG. 9 illustrates a further appliance which is similar to that of FIG. 8 and like parts have again been indicated by like reference numerals. In this case the ribs 14B are of equal width and are both provided with flaps 50 which fold down against the rims of the ribs and are provided with tongues 52 which fit together into the channel between the ribs. The outer edge of one flap has a longitudinally extending V-shaped tongue 53 which fits into a mating V-groove 54 in the outer edge of the other flap to lock the two flaps together. In the applied condition the overall configuration of this appliance is essentially identical with that of FIGS. 7 and 8.

In all of the illustrated embodiments of the invention the line of incision lies in a common neutral plane of the tape member 11 and spring member 12 and the appliance can bend in two planes without applying disturbing forces to the skin in the region of the incision. The appliance can therefore permit normal skin movements in the vicinity of the incision while, for the reasons explained above, it firmly holds the two areas of skin adjacent the incision against movement relative to one another. However, these particular constructions have been advanced by way of example only and it is to be understood that many modifications and variations could be made without departing from the scope of the appended claims.

I claim:

1. A surgical appliance comprising an elongate flexible tape member and an elongate spring member; said tape member having on one side an adhesive surface by which it can be adhered to the skin of a surgery patient and on the other side a pair of parallel ribs extending longitudinally of the tape member and defining between them a course along which to make an incision through the tape member and the skin beneath; said spring member comprising two sets of aligned straight side portions interconnected by connecting portions such that the spring member is of generally channel shaped configuration with said sets of straight side portions defining the mouth of the channel; said spring member being applicable to the tape member such that the ribs project into said channel shaped configuration of the channel member and are clasped between said sets of straight side portions; and said connecting portions of the spring member being formed with tongues to fit between said ribs when the spring member is applied to the tape member so as to engage the ribs and restrain them against laterally inward movement relative to one another.

2. A surgical appliance comprising an elongate flexible tape member and an elongate spring member; said tape member having on one side an adhesive surface by which it can be adhered to the skin of a surgery patient and on the other side a pair of parallel ribs extending longitudinally of the tape member and defining between them a course along which to make an incision through the tape member and the skin beneath; said spring member comprising two sets of aligned straight side portions interconnected by connecting portions such that the spring member is of generally channel shaped configuration with said sets of straight side portions defining the mouth of the channel; and said spring member being applicable to the tape member such that the ribs project into said channel shaped configuration of the spring member and are clasped between said sets of straight side portions, said ribs being shaped to define at their outer sides a pair of longitudinally extending and laterally outwardly facing channels for engagement with the two sets of straight side portions of the spring member when the spring member is applied to the tape member, said tape member including a flat base strip from a face of which the ribs project and the ribs have inner portions by which they are connected to the base strip and outer portions which project laterally outwardly from the inner portions such that said laterally outwardly facing channels are defined between the outer portions of the ribs and said face of the base strip, said straight side portions of the spring member and said outwardly facing channels of the tape member interengage with an interference fit, said connecting portions of the spring member engage the rims of the ribs when the spring member is applied to the tape member to provide gripping action on the ribs between said rib rims and the channels, and tongues formed in the connecting portions of the spring member to fit between said ribs and restrain them against laterally inward movement relative to one another when the spring member is applied to the tape member.

3. A surgical appliance comprising an elongate flexible tape member and an elongate spring member; said tape member having on one side an adhesive surface by which it can be adhered to the skin of a surgery patient and on the other side a pair of parallel ribs extending longitudinally of the tape member and defining between them a course along which to make an incision through the tape member and the skin beneath; said spring member comprising two sets of aligned straight side portions interconnected by connecting portions such that the spring member is of generally channel shaped configuration with sets of straight side portions defining the mouth of the channel; said spring member being applicable to the tape member such that the ribs project into said channel shaped configuration of the spring member and are clasped between said sets of straight side portions; and said tape member further including flap means to fold against the rims of the ribs and carrying tongue means to engage between the ribs and restrain them against laterally inward movement relative to one another when the spring member is applied to the tape member.

4. A surgical appliance as claimed in claim 3, wherein said flap means is a flap hingedly connected to one of said ribs to fold against the rims of the ribs and having a tongue to fit between the ribs so as to provide the restraining action.

5. A surgical appliance as claimed in claim 4, wherein the flap also includes an outer edge flange to engage the other of the ribs to restrain the ribs against lateral separation.

6. A surgical appliance as claimed in claim 3, wherein said flap means is a pair of flaps connected one to each of the ribs to fold against the rims of the ribs and each having a tongue to engage between the ribs.

7. A surgical appliance as claimed in claim 3, wherein said connecting portions of the spring member engage the flap means with an interference fit when the spring member is applied to the tape member.

8. A surgical appliance comprising an elongate flexible member and an elongate spring member; said tape member having on one side an adhesive surface by which it can be adhered to the skin of a surgery patient and on the other side a pair of parallel ribs extending longitudinally of the tape member and defining between them a course along which to make an incision through the tape member and the skin beneath; said spring member comprising the sets of aligned straight side portions interconnected by connecting portions such that the spring member is of generally channel shaped configuration with said sets of straight side portions defining the mouth of the channel; and said spring member being applicable to the tape member such that the ribs project into said channel shaped configuration of the spring member and are clasped between said sets of straight side portions, wherein the two sets of straight side portions of the spring member are staggered relative to one another in the longitudinal direction of the spring member and said connecting portions are successively oppositely inclined to the longitudinal direction of the spring member with each straight portion which is overlapped in the longitudinal direction by a pair of the straight portions of the other set being connected to the adjacent ends of that pair by two mutually oppositely inclined straight portions, whereby axial compression of the spring member causes the two sets of straight portions to move toward one another.

9. A surgical appliance as claimed in claim 8, wherein the connecting portions of the spring member are successively equally and oppositely inclined to the longitudinal direction of the spring member.

10. A surgical appliance as claimed in claim 8, wherein the spring member has two end portions disposed on a longitudinal central plane of the spring member such that the spring member can be axially compressed by tensioning a thread between those end portions.

11. A surgical appliance as claimed in claim 8, wherein the straight side portions of each said set traverse a major proportion of the overall length of the set when the spring member is in its relaxed condition.

12. A surgical appliance as claimed in claim 8, wherein the straight side portions of each set traverse at least 75% of the overall length of the set when the spring member is in its relaxed condition.

13. A surgical appliance as claimed in claim 12, wherein said tape member comprises a flat base strip having said adhesive surface on one face thereof and said ribs project from the other face of the base strip; said ribs have inner portions by which they are connected to the base strip and outer portions which project laterally outwardly from the inner portions such that a pair of longitudinally extending, laterally outwardly facing channels are defined at the outer sides of the ribs between the outer portions of the ribs and said other face of the base strip; said straight side portions of the spring member are cylindrical and the roots of said laterally outwardly facing channels are cylindrically curved to suit.

14. A surgical appliance as claimed in claim 13, wherein said connecting portions of the spring member engage the rims of the ribs when the spring member is applied to the tape member to provide gripping action on the ribs between said rib rims and said laterally outwardly facing channels.

* * * * *